(12) United States Patent
Ogden

(10) Patent No.: US 6,299,645 B1
(45) Date of Patent: Oct. 9, 2001

(54) DOVE TAIL TOTAL KNEE REPLACEMENT UNICOMPARTMENTAL

(76) Inventor: William S. Ogden, 101 N. Madison St., Whiteville, NC (US) 28472

( * ) Notice: Subject to any disclaimer, the term of this patent is extended or adjusted under 35 U.S.C. 154(b) by 0 days.

(21) Appl. No.: 09/359,974

(22) Filed: Jul. 23, 1999

(51) Int. Cl.$^7$ .................................................. A61F 2/38
(52) U.S. Cl. ..................... 623/20.21; 623/20.32; 623/20.35
(58) Field of Search ............... 623/20.14, 20.15, 623/20.21, 20.28, 20.29, 20.3, 20.31, 20.32, 20.33, 20.34, 20.35, 20.36

(56) References Cited

U.S. PATENT DOCUMENTS

| | | | |
|---|---|---|---|
| 3,715,763 | * 2/1973 | Link | 623/20.3 |
| 3,964,106 | 6/1976 | Hutter et al. | 3/1.911 |
| 4,034,418 | * 7/1977 | Jackson et al. | 623/20.3 |
| 4,193,140 | * 3/1980 | Treace | 623/20.14 |
| 4,340,978 | 7/1982 | Buechel et al. | 3/1.911 |
| 4,470,158 | 9/1984 | Pappas et al. | 3/1.911 |
| 4,659,331 | * 4/1987 | Matthews et al. | 623/20.21 |
| 4,711,639 | * 12/1987 | Grundei | 623/20.31 |
| 4,795,468 | * 1/1989 | Hodorek et al. | 623/20.28 |
| 4,838,891 | * 6/1989 | Branemark et al. | 623/20.3 |
| 4,919,671 | * 4/1990 | Karpf | 623/20.3 |
| 5,092,895 | * 3/1992 | Albrektsson et al. | 623/20.3 |
| 5,207,711 | 5/1993 | Caspari | 623/20 |
| 5,336,266 | * 8/1994 | Caspari et al. | 623/20.35 |

* cited by examiner

Primary Examiner—David J Isabella
(74) Attorney, Agent, or Firm—Sheldon H. Parker

(57) ABSTRACT

A knee joint prosthesis is provided for implanting on the tibial plateau and femoral condyle of the knee. The prosthesis includes a tibial prosthesis having a tibial fixation surface on the tibial prosthesis adapted to be positioned on the tibial plateau. The tibial fixation surface has at least one tibial attachment means for securing the tibial prosthesis to the tibial plateau. It further includes a femoral prosthesis having a femoral fixation surface adapted to be positioned on the femoral condyle. The femoral fixation surface has at least one femoral attachment means for securing the femoral prosthesis to the femoral condyle. The prosthesis further includes a bearing member supported by the tibial prosthesis for engaging the femoral prosthesis in weight bearing relationships.

17 Claims, 7 Drawing Sheets

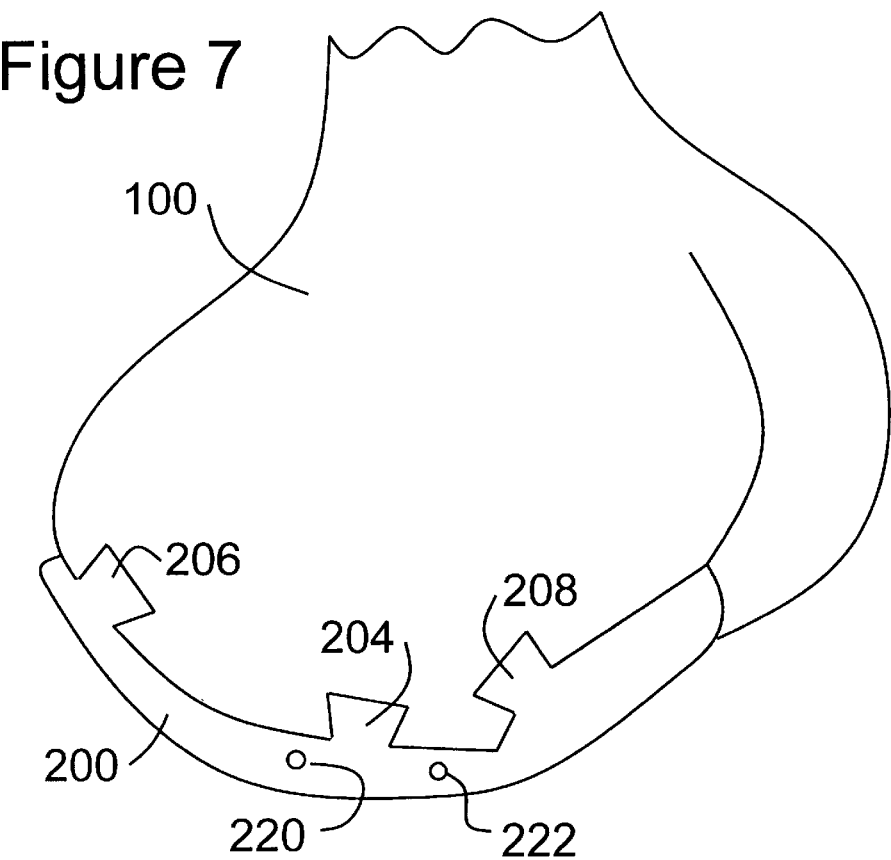

DOVE TAIL TOTAL KNEE REPLACEMENT UNICOMPARTMENTAL

BACKGROUND OF THE INVENTION

1. Field of the Invention

The present invention relates primarily to an improved prosthesis of unicompartmental total knee replacement to both the femur and to the tibial, and more specifically to a special dove tail extension from the prosthesis.

2. Brief Description of the Prior Art

Resurfacing or replacement of one component of the knee is not a new concept. It is widely recognized that there are three components to the knee, the medial compartment, lateral compartment and the patellofemoral compartment. "Tibial Plateau Prosthesis," by McKeever, D. C. (Clin. Othrop., 18:86–95, 1960) and "The use of Hemiarthroplasty Prosthesis for Advanced Osteoarthritic and Rheumatoid arthritis of the knee," by MacIntosh, D. I. and Hunter, G. A. (J. Bone Joint Surgery, 54-B(2): 244–255, 1972) reported on the insertion of the prosthetic disc into the worn out tibial plateau "Unicompartmental Knee Replacement," by Marmor, L. (In Total Knee Arthroplasty, pp. 245–280. Edited by J. A. Rand. New York, Raven Press, 1993). Early total knee designs consisted of constraining unicompartmental replacements and preceded the accepted form of the total knee as now known as a Duocondylar total prosthesis as described in "Historical Development, Classification, and Charackteristics of Knee Prostheses," by Insall, J. N. (In Surgery of the Knee, pp. 677–717. Edited by J. N. Insall. New York, Chruchill Livingstone, 1993).

Through the unicompartmental design described in "Die Schlittnprothese, eine Teiiprothese bei Zerstorungen im Kniegelenk," by Engelbrecht, E. (Chirurg, 42: 510–514, 1971) added a true polycentric femoral component and "Unicompartmental Knee Replacement," by Marmor, L. (Total Knee Arthroplasty pp. 245–280. Edited by J. A. Rand. New York, Raven Press, 1993) added a so called modularity to the tibia component in the sense of providing different plateau thicknesses. "Clinical Results of the Oxford Knee. Surface arthroplasty of the Tibiofomoral Joint with a Meniscal Bearing Prosthesis," by Goodfellow, J. W. and O'Connor, J. (Clin. Orthop., 205:21–42, 1988) provided a so called meniscal bearing plateau. For the last twenty years, candidates for the unicompartmental knee have done well with this prosthesis, however breakage of the prosthesis and early wear of the bearing surface have caused many surgeons to avoid the unicompartmental replacement, instead doing a complete total knee, even though only one of the three joints of the knee was involved. It has been found that the bone on the effected side, usually the medial side of the joint is very thick and hardened with eburnation and this may be the hardest bone in the body. With this very hard bone, it is felt that minimal resection would keep the prosthesis from subsiding or sinking into the softer bone beneath, and for that reason as little bone as possible is resected from both the tibial and the femur at the time of insertion of the prosthesis.

The designs of the unicompartmental replacement do very well. The Marmor knee prosthesis which was introduced in the early seventies, featured a polyethylene component that is inserted into the tibial plateau. It was designed to be nestled in cancellous bone within the cortical rim while in many current designs the tibial component is meant to rest on the cortical bone such as the prosthesis that is now being described. Like the prosthesis of "The use of Hemiarthroplasty Prosthesis for Advanced Osteoarthritic and Rheumatoid arthritis of the knee," by MacIntosh, D. I. and Hunter, G. A. (J. Bone Joint Surgery, 54-B(2): 244–255, 1972), the Marmor tibial component had no peg and therefore had no way of having stabilization for the tibial prosthesis "Unicondylar Knee Arthroplasty. 2–10 Year Follow-Up Evaluation," by Cartier, P. and Choaib S. (J. Arthroplasty, 2: 157–162, 1987).

Most implants however had one or two pegs, and one manufacturer had added a small "X" shaped peg. As with a total knee replacement, tibial components can be all polyethylene or metal backed. Some designers have returned to the all polyethylene tibial component while others consider the modular metal back systems to be safer and more beneficial. Unicompartmental tibial components can be inserted with or without cement and are available in modular or one piece designs, or available with a fixed or mobile tray as described in "Mensical-Bearing Unicompartmental Knee Arthroplasty. An 11-year Clinical Study," by Cohen, M., Buechel, F. and Pappas, M. J. (Orthop. Rev., 20:443–448, 1991). U.S. Pat. No. 5,207,711 utilizes both the cement-securing method and other securing devices (screws in that patent) to secure the prosthesis. The '711 patent describes the common problems that arise due to the use of cement, such as misalignment, anchoring problems, and the escape of excess cement that can lead to crumbling (and therefore irritation) and jeopardize the integrity of the cemented parts.

The femoral component of the unicompartmental prosthesis can be made of the resurfacing type which necessitates resection of only a few millimeters of the posterior condyle, or it can be more of a total knee type which necessitates condylar resection such as distal, posterior and chamfer cuts. Femoral components can be inserted with or without cement. A number of unicompartmental replacements look like half of the parent total knee system that are now present and instrumentation is similar as described in "Universal Intramedullary Instrumentation for Unicompartmental Total Knee Arthroplasty," by Bert, J. M. (Clin. Orthop., 271: 79–87, 1991. It should be noted that the reported results of unicompartmental replacements have varied with the type of implant and from surgeon to surgeon. The results are to be examined in light of the operative alternatives and the ease or the difficulty once the prosthesis can be revised or converted to a total knee replacement. "Unicompartmental Tibiofemoral Resurfacing Arthroplasty," by Laskin, R. S. (J. Bone and Joint Surgery, 60-A: 182–185, March 1978) found that only 65 percent of 37 knees had satisfactory relief from pain at two years and "Unicompartmental Knee Arthroplasty. Ten- to 13-year follow-up study," by Marmor, L. (Clin. Orthop., 226: 14–20, 1988) reported to find 21 failures in 60 knees. He thought these failures were due mostly to an excessively thin tibial component, (6 millimeters) and by the standards of today, poor selection of patients. "Unicompartmental Knee Arthroplasty. Eight- to 12-year Follow-Up Evaluation with Survivorship Analysis," by Scott, R. D., Cobb, A. G., McQueary, F. G. and Thornhill, T. S. (Clin. Orthop., 271: 96–100, 1991) however found that in 100 consecutive unicompartmental replacements, 85 percent had survived 10 years and "Unicompartmental Knee Arthroplasty. A Multicenter Investigation with Long-Term Follow-Up Evaluation," by Hock, D. A., Marmor, L., Gibson, A. and Rougraff, B. I. (Clin. Orthop., 286: 154–159, 1993) reported that 91 percent of 294 implants had survived for over 10 years "Unicompartmental Knee Replacement," by Marmor, L. (In Total Knee Arthroplasty, pp. 245–280. Edited by J. A. Rand. New York, Raven Press, 1993). Therefore the prosthesis itself and the concept that unicompartmental knees are widely accepted and is seen as a beneficial adjunct to the treatment of severe arthritis of the knee.

SUMMARY OF THE INVENTION

A knee joint prosthesis is provided for implanting on the tibial plateau and femoral condyle of the knee. The prosthesis includes a tibial prosthesis having a tibial fixation surface on the tibial prosthesis adapted to be positioned on the tibial plateau. The tibial fixation surface has at least one tibial attachment means for securing the tibial prosthesis to the tibial plateau. It further includes a femoral prosthesis having a femoral fixation surface adapted to be positioned on the femoral condyle. The femoral fixation surface has at least one femoral attachment means for securing the femoral prosthesis to the femoral condyle. The prosthesis further includes a bearing member supported by the tibial prosthesis for engaging the femoral prosthesis in weight bearing relationships.

The tibial prosthesis further includes a bearing member fixation surface having a central recess with at least one adjoining recess. The central recess is adapted to receive the bearing member. Each of the at least one adjoining recesses, receive one of at least one clip member. The at least one clip member is attached to the bearing member.

At least one tibial attachment means extends from the tibial fixation surface and is adapted to be embedded in the tibial plateau. The tibial attachment means is dovetail in structure. The tibial attachment means has a tibial top side directly ill contact with the tibial prosthesis and a tibial bottom side opposite the tibial top side. The tibial bottom side connected to the tibial top side by two tibial sloped sides.

The dovetailed of the tibial attachment means is about one third of an inch deep between the tibial top side and the tibial bottom side, about two tenths of an inch wide at the tibial top side of the at least one tibial attachment means, and form on the order of about 60 degree angles between the two tibial sloped sides form and the tibial fixation surface. These dimensions are preferred dimensions and angles, but there is latitude to vary these dimension, as known to those skilled in the art.

At least one femoral attachment means extends from the femoral fixation surface and is embedded in the femoral condyle.

At least one hole can be provided in the femoral prosthesis for attachment elements.

The prosthesis implantation method includes the following steps:

the tibial plateau is resected to form a at least one tibial groove so as to receive each tibial attachment means of a tibial prosthesis to secure the tibial prosthesis to the tibial plateau, the femoral condyle is resected to form a at least one femoral groove so as to receive each femoral attachment means of a femoral prosthesis to secure the femoral prosthesis to the femoral condyle, the tibial attachment means of the tibial prosthesis is inserted into the at least one tibial groove resected in the tibial plateau, the femoral attachment means of the femoral prosthesis is inserted into the at least one femoral groove resected in the femoral condyle, a bearing member is inserted into a central recess on the tibial prosthesis and is supported by the tibial prosthesis for engaging the femoral prosthesis in weight bearing relationships thereby enabling the implantation of the prosthesis.

The method of prosthesis implantation method is, in greater detail, as follows:

the tibial plateau is resected to form a at least one dovetailed tibial groove so as to receive each dovetailed tibial attachment means of a tibial prosthesis to secure the tibial prosthesis to the tibial plateau, the femoral condyle is resected to form a at least one dovetailed femoral groove so as to receive each dovetailed femoral attachment means of a femoral prosthesis to secure the femoral prosthesis to the femoral condyle, the tibial attachment means of the tibial prosthesis is inserted into the at least one dovetailed tibial groove resected in the tibial plateau, the femoral attachment means of the femoral prosthesis is inserted into the at least one dovetailed femoral groove resected in the femoral condyle, a bearing member is inserted into a central recess on the tibial prosthesis and is supported by the tibial prosthesis for engaging the femoral prosthesis in weight bearing relationships, the tibial prosthesis having a bearing member fixation surface consisting of a central recess with at least one adjoining recess, the central recess to receive the bearing member, and the at least one adjoining recess to each receive one of at least one clip member, the at least one clip member being attached to the bearing member thereby enabling the implantation of the prosthesis.

BRIEF DESCRIPTION OF THE DRAWINGS

FIG. 7 is a perspective view of the femur of FIG. 1 and the prosthesis of FIG. 2 dove tailed together.

DESCRIPTION OF THE PREFERRED EMBODIMENTS OF THE INVENTION

Figure 1:
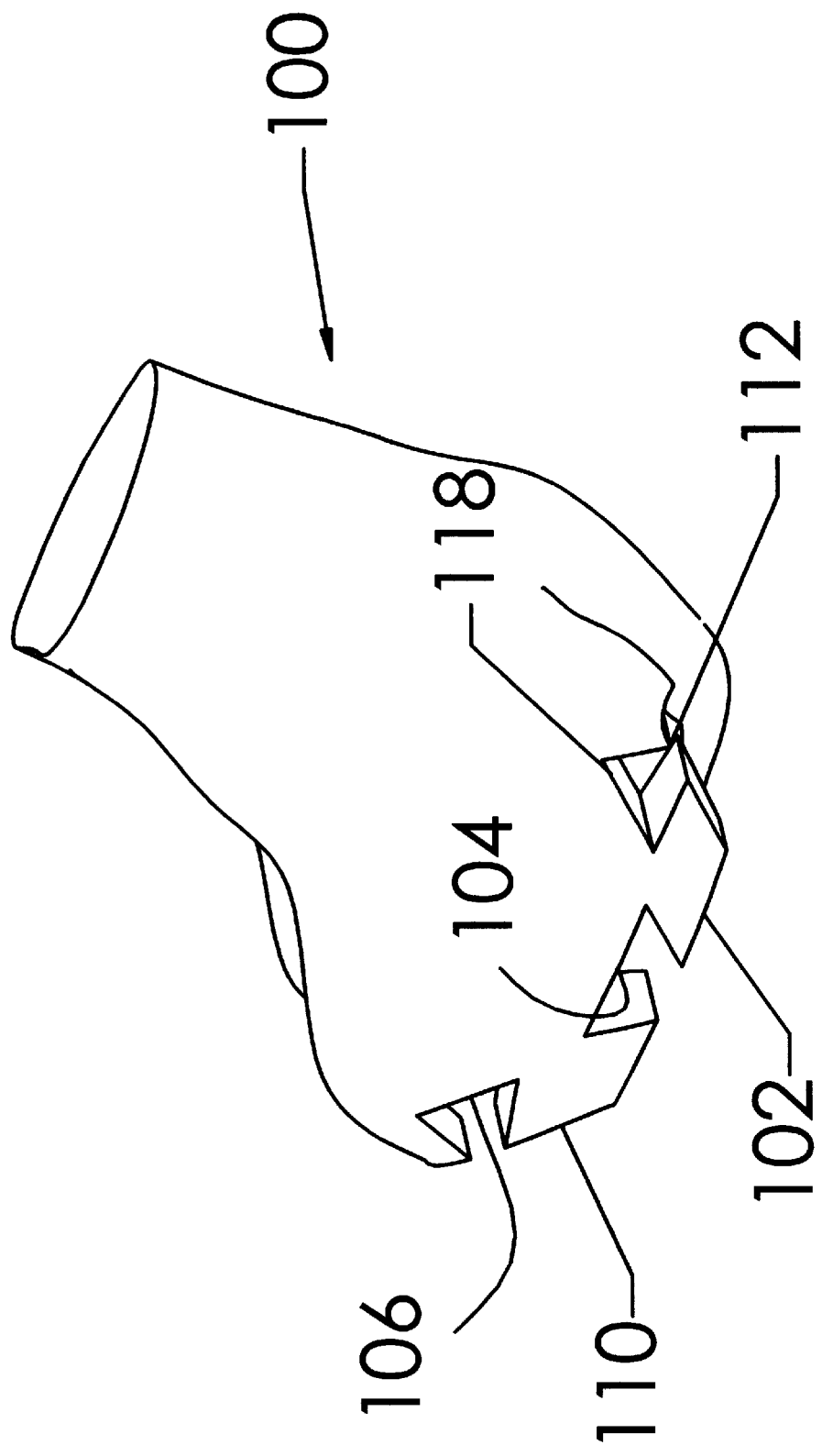
FIG. 1 is a perspective view of a femur which has been cut to provide dove tails grooves.

Description of the Present Prosthesis and Rationale

The prosthesis is designed primarily so that the eburnated bone on the medial femoral condyle and the medial tibial will require minimal bone resection, therefore allowing the very hard eburnated bone to give good support for the prosthesis. In addition the dove tail, or the I beam, extension from both the tibial and the femoral prosthesis will add significantly to the strength of the base plate of the prosthesis. The dove tail structure would be approximately trapezoidal in shape, with the smaller end contacting the remainder of the prosthesis, with the sloped sides extending outward. This is a contact bearing type of prosthesis with the femur being titanium and the tibia being titanium with a polyethylene bearing surface.

Preferably, no methylmethacrylate will need to be used with this particular prosthesis and it will be fabricated in such a way that hydroxyapatite and ingrowth metal will be associated with the press fit design.

The present prosthesis that is being described consists of two parts, both being made of titanium with a bearing surface made of polyethylene. It is planned this will be a press fit type with hydroxyapatite present with ingrowth potential, both for the tibia and femur.

The Femoral Prosthesis

The femoral prosthesis is of a blade type that will require minimal resection of bone from the eburnated or hardened bone on the medial side of the femur. It will be inserted from the medial side, rather than the dorsal side of the knee. The fitting chamfer cuts will be made from the medial side of the femur and the prosthesis will then be inserted from the more medial side of the knee and hammered home. The method of attachment will be three dove tail type attachments of the prosthesis. These dove tails are made integral with the prosthesis itself.

The dove tails will be separated in such a way that the very hardened bone will be present between the dove tails and will allow early fixation to the femur. These dove tails will extend across the entire width of the femoral prosthesis. Please note the enclosed drawings to show the placement of these dove tails and their appropriate size. Once this is hammered home the stability will be enhanced by the roughened surface of the hydroxyapatite and early osteosynthesis should occur within the first 2–4 weeks.

The Tibial Prosthesis

The tibial prosthesis is made of titanium with dove tail extending its entire width in the AP diameter, and this will be hammered into a prepared bed produced with a special dove tail reamer. This dove tail reamer will be slightly smaller than the dove tailed extension on the tibial prosthesis, which will allow a tight fit and earlier osteo integration. Minimal bone will be resected from the tibia and special instruments will be provided which will allow the dove tail reamer to cut a very precise dove tail into the hardened bone.

The tibial prosthesis will be inserted from the anterior posterior direction and the size of the insert determined at the time of surgery with care being made to avoid overcorrection of the knee deformity.

The weight bearing surface will be polyethylene and press fitted into the prosthesis. The minimal thickness will be 8 millimeters. There will be thickness ranging from 8, 9, 10, 12, 14 millimeters in size. Accompanied drawings show precisely the size and methodology from which this will be inserted.

The present invention recognizes that unicompartmental prostheses indeed are a very vital part in the surgical treatment of degenerative and rheumatoid arthritis. It should be recognized that the advantages of this prosthesis include the following:

1. Minimal bone resection. It is felt that only approximately 2–3 millimeters of bone should be resected from the femur and from the tibia.
2. Superior fixation secondary to the dove tailing will allow early motion and excellent stability.
3. The strength of the prosthesis will be markedly improved by the I beam construction of the dove tails.
4. Minimal soft tissue dissection will be necessary for the insertion and the application of this prosthesis.
5. This prosthesis lacks a need for the ubiquitously present cement or securing devices (such as screws, etc.) found in other prostheses, and therefore avoids the problems that arise from the use of cement, such as misalignment, anchoring, and deterioration which may lead to irritation and jeopardized integrity.

As shown in FIG. 1, a femur indicated generally as 100, is provided with a plurality of dove tail grooves, preferably, three dove tail grooves, 104, 106 and 108. The lower most surfaces of the femur are cut to provide planar surfaces 102, 112 and 110, to match with the corresponding surfaces of the femoral prosthesis.

Figure 2:
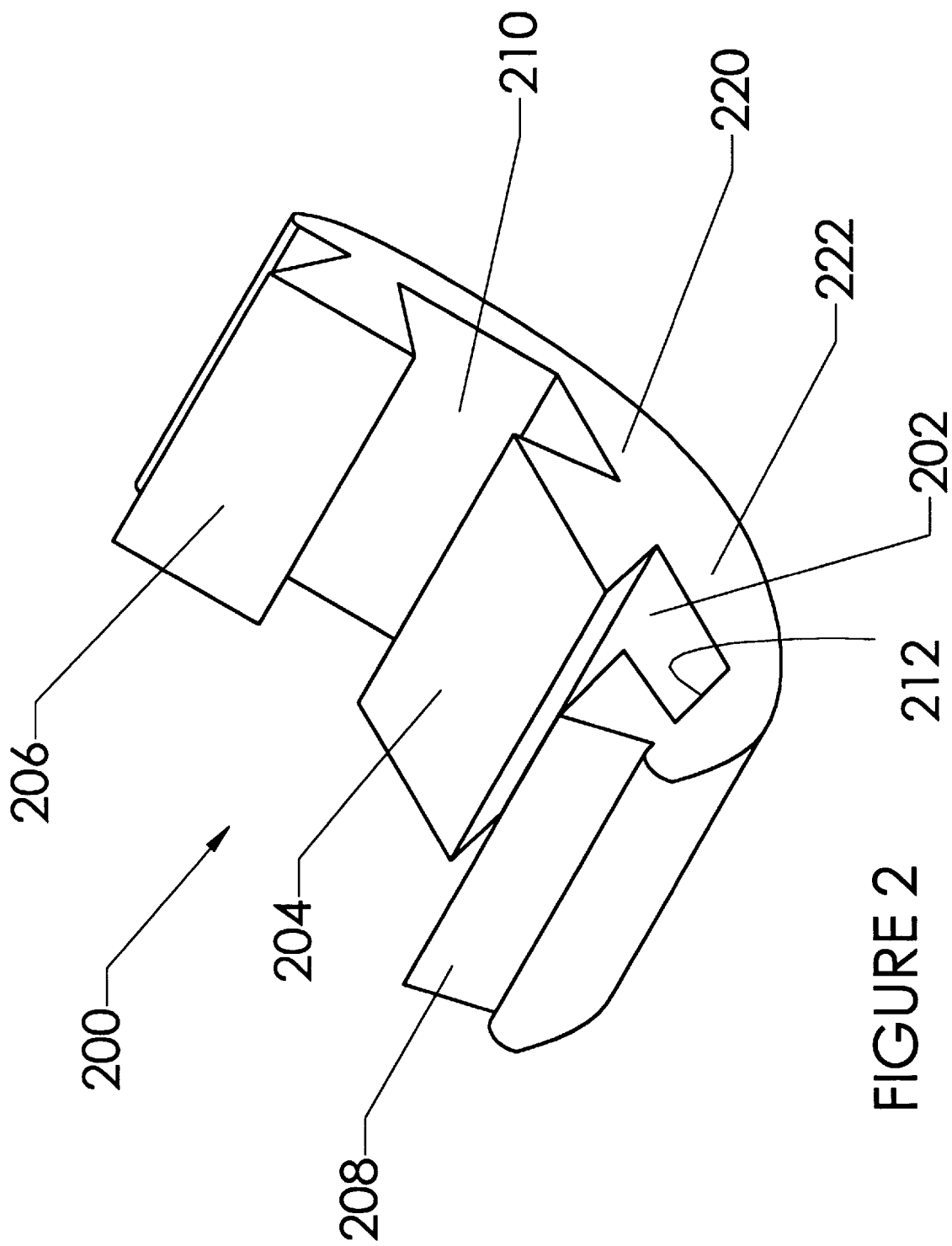
FIG. 2 is a perspective view of the femoral prosthesis, having dove tails conforming to the dove tails grooves in the femur of FIG. 1.

As shown in FIG. 2, the femoral prosthesis indicated generally as 200, has the corresponding number of dove tails, 204, 206 and 208 corresponding in size, shape and position to the dove tail grooves, 104, 106 and 108, respectively. The planar surfaces of the femoral prosthesis 210, 202 and 212, correspond exactly to the corresponding planar surfaces 110, 102 and 112 which have been cut on the femur. Holes 220 and 222 provide for the attachment elements, which are typically pins, as well known in the art. The dove tails have a pair of 60 degree angles and a two tenths of an inch small side. The distance between the small side and the parallel wider side is one third of an inch. Advantageously, each of the three dove tails have approximately the same dimensions.

Figure 3:
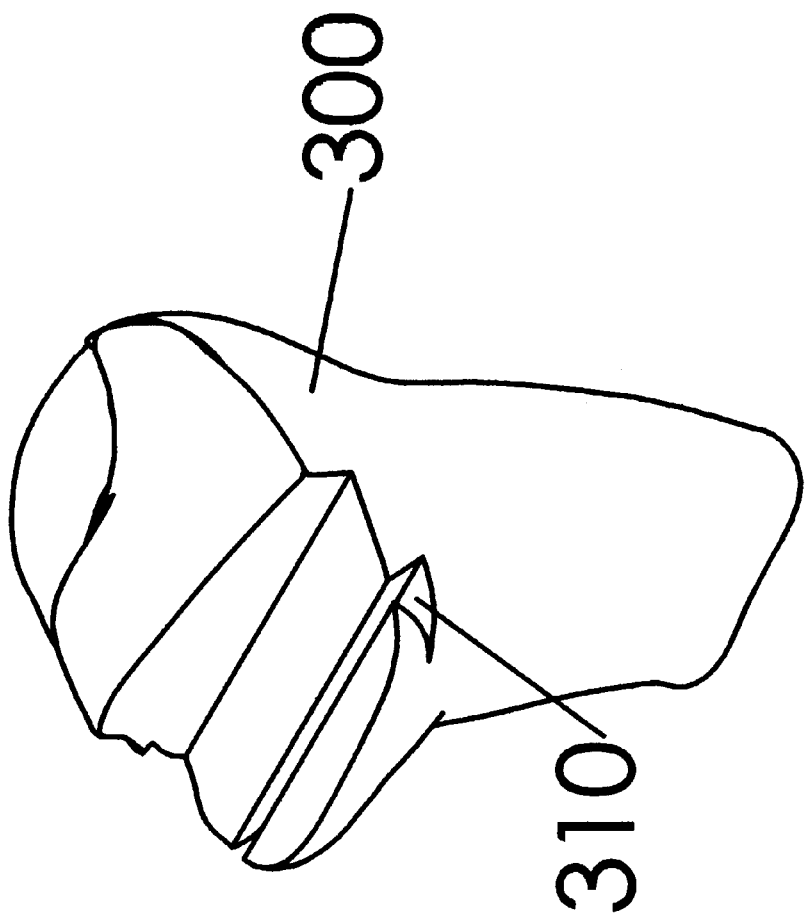
FIG. 3 is a perspective view of a tibia which has been cut to provide a plateau and a dove tail groove.
Figure 4:
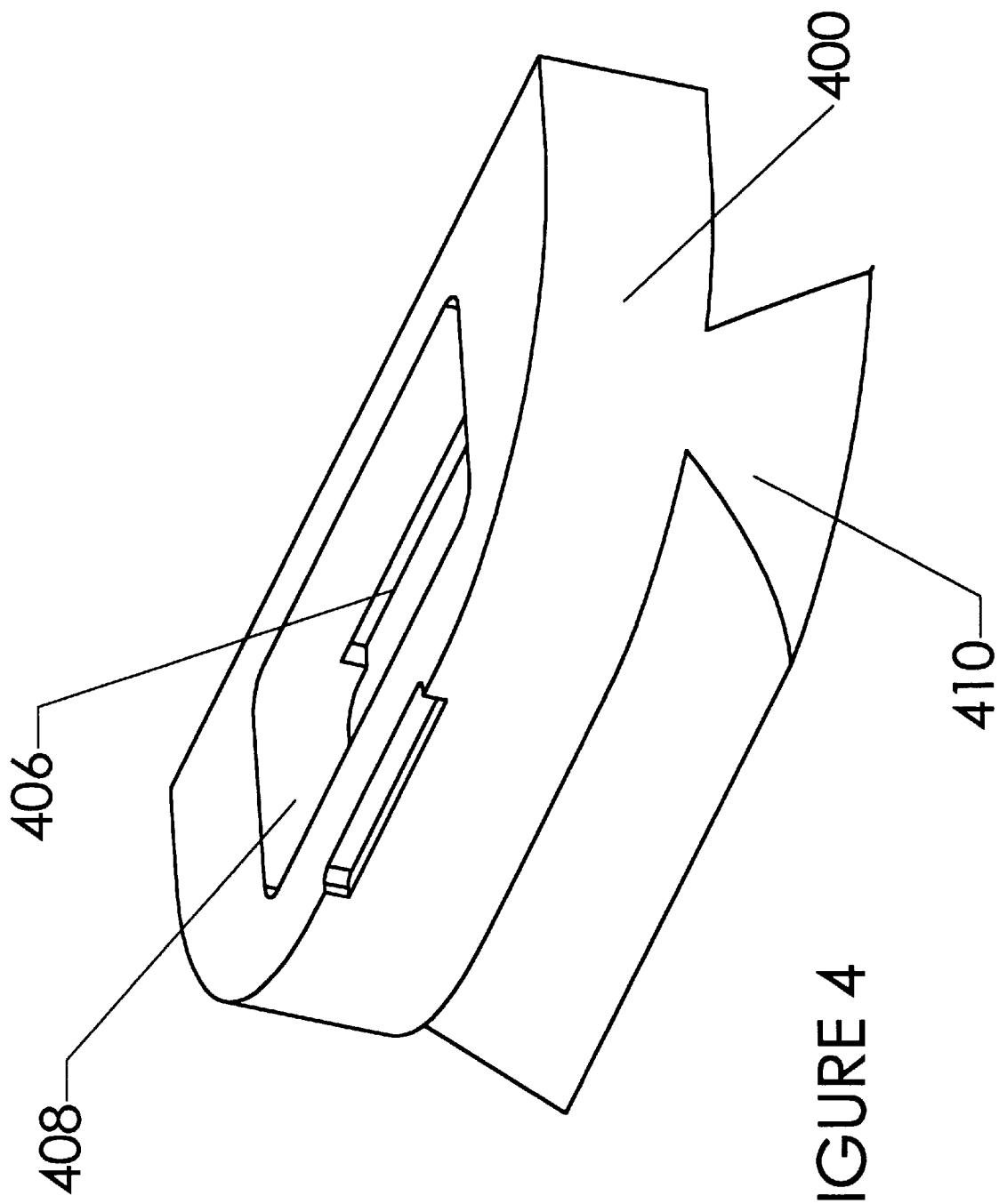
FIG. 4 is a perspective view of a tibia prosthesis having a dove tail confroming to the dove tail groove in the tibia of FIG. 3.
Figure 5:
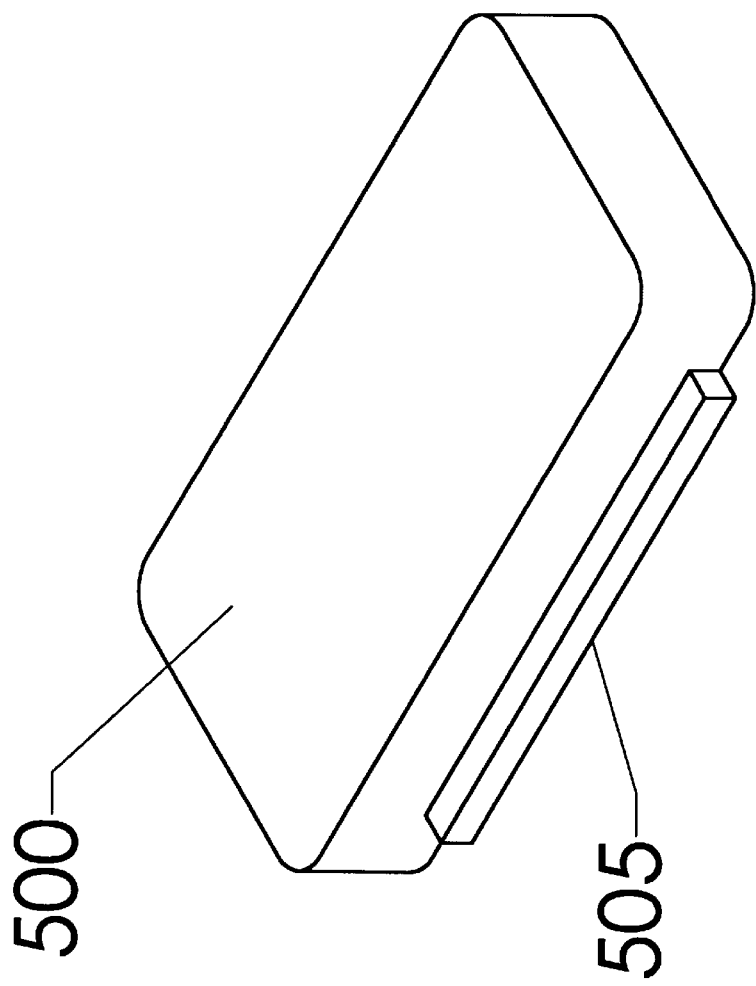
FIG. 5 is a perspective view of the bearing surface which clips into the prosthesis of FIG. 4.

The tibia 300, of FIG. 3, is provided with a medial tibial plateau, and a dove tail groove 310. The tibial prosthesis 400 has a dove tail 410, which corresponds exactly, in size, shape and position, to the dove tail groove 310 which has been reamed in the tibia. The tibial prosthesis is provided with a central recess 408, for receiving a bearing member, 500. A pair of undercuts, or recesses 406 are provided, only one of which can be seen in FIG. 4. The second undercut receives the clip member 505, of the bearing member 500, of FIG. 5. A pair of clip members are provided on the bearing member to correspond to the pair of recesses in the tibial prosthesis. The bearing member is an ultra high molecular weight polyethylene, (UHMWPE). The dovetail 410 is advantageously one third of an inch deep and two tenths of an inch wide at the top side of the trapezoid which contains the dovetail. The two lower angles are 60 degrees.

Figure 6:
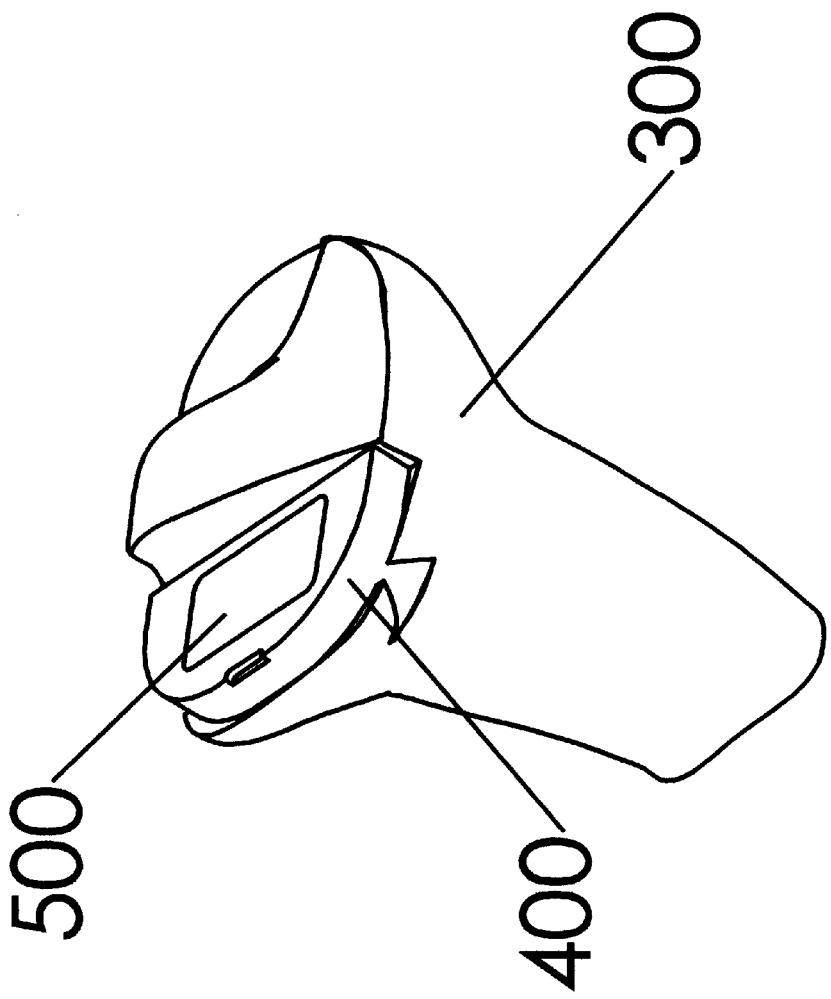
FIG. 6 is a perspective view of the tibia of FIG. 3, with the prosthesis of FIG. 4 and the bearing surface of FIG. 5, in their respective assembled positions.

In FIG. 6 the tibial prosthesis 400 is inserted from the anterior posterior direction into the tibia 300. The weight bearing surface 500 is press fitted into the prosthesis 400.

In FIG. 7 the femoral prosthesis 200 is inserted from the medial side into the femur 100. The prosthesis 200 is attached by the three dove tails 206, 204 and 208 of the prosthesis 200. Holes 220 and 222 provide for the attachment elements.

What is claimed is:

1. A knee joint prosthesis for implant on the tibial plateau and femoral condyle of the knee comprising:
    a tibial prosthesis, a tibial fixation surface on said tibial prosthesis adapted to be positioned on the tibial plateau, said tibial fixation surface having a at least one tibial attachment means for securing said tibial prosthesis to the tibial plateau,
    a femoral prosthesis, a femoral fixation surface on said femoral prosthesis adapted to be positioned on the femoral condyle, said femoral fixation surface having a at least one femoral attachment means for securing said femoral prosthesis to the femoral condyle,
    a bearing member supported by said tibial prosthesis for engaging said femoral prosthesis in weight bearing relationships.

2. A knee joint prosthesis as recited in claim 1 wherein said tibial prosthesis further comprises a bearing member fixation surface having a central recess with at least one adjoining recess, said central recess being adapted to receive said bearing member, and said at least one adjoining recess to each receive one of at least one clip member, said at least one clip member being attached to said bearing member.

3. A knee joint prosthesis as recited in claim 1 wherein said at least one tibial attachment means extending from said tibial fixation surface adapted to be embedded in the tibial plateau.

4. A knee joint prosthesis as recited in claim 3 wherein said tibial prosthesis further comprising a bearing member fixation surface, said bearing member fixation surface having a central recess with at least one adjoining recess, said central recess being adapted to receive said bearing member, and said at least one adjoining recess being adapted to each receive one of at least one clip member, said at least one clip member being attached to said bearing member.

5. A knee joint prosthesis as recited in claim 3 wherein said at least one tibial attachment means is dovetailed in structure, with a tibial top side of said at least one tibial attachment means being that which is directly in contact with the tibial prosthesis, a tibial bottom side opposite said tibial top side, said tibial bottom side connected to said tibial top side by two tibial sloped sides.

6. A knee joint prosthesis as recited in claim 5 wherein said tibial prosthesis has a bearing member fixation surface consisting of a central recess with at least one adjoining recess, said central recess to receive said bearing member, and said at least one adjoining recess to each receive one of at least one clip member, said at least one clip member being attached to said bearing member.

7. A knee joint prosthesis as recited in claim 5 wherein said dovetailed at least one tibial attachment means is about one third of an inch deep between said tibial top side and said tibial bottom side, about two tenths of an inch wide at said tibial top side of said at least one tibial attachment means, and form on the order of about 60 degree angles between said two tibial sloped sides form and said tibial fixation surface.

8. A knee joint prosthesis as recited in claim 7 wherein said tibial prosthesis has a bearing member fixation surface, said bearing member fixation surface having a central recess with at least one adjoining recess, said central recess being adapted to receive said bearing member, and said at least one adjoining recess being adapted to each receive one of at least one clip member, said at least one clip member being attached to said bearing member.

9. A knee joint prosthesis as recited in claim 1 wherein said femoral prosthesis has at least one hole, said at least one hole being provided for attachment elements.

10. A knee joint prosthesis as recited in claim 1 wherein said at least one femoral attachment means extends from said femoral fixation surface and is embedded in the femoral condyle.

11. A knee joint prosthesis as recited in claim 10 wherein said femoral prosthesis has at least one hole, said at least one hole being provided for attachment elements.

12. A knee joint prosthesis as recited in claim 10 wherein said at least one femoral attachment means is dovetailed in structure, with a femoral top side of said at least one femoral attachment means being that which is directly in contact with the femoral prosthesis, a femoral bottom side opposite said femoral top side, said femoral bottom side connected to said femoral top side by two femoral sloped sides.

13. A knee joint prosthesis as recited in claim 12 wherein said femoral prosthesis has at least one hole, said at least one hole being provided for attachment elements.

14. A knee joint prosthesis as recited in claim 12 wherein said dovetailed at least one femoral attachment means is about one third of an inch deep between said femoral top side and said femoral bottom side, about two tenths of an inch wide at said femoral top side of said at least one femoral attachment means, and form about 60 degree angles between said two femoral sloped sides form and said femoral fixation surface.

15. A knee joint prosthesis for implant on the tibial plateau and femoral condyle of the knee comprising:

a tibial prosthesis, a tibial fixation surface on said tibial prosthesis adapted to be positioned on the tibial plateau, said tibial fixation surface having at least one tibial attachment means for securing said tibial prosthesis to the tibial plateau, said at least one tibial attachment means extending from said tibial fixation surface to be embedded in the tibial plateau, said at least one tibial attachment means is dovetailed in structure, with a tibial top side of said at least one tibial attachment means being that which is directly in contact with the tibial prosthesis, a tibial bottom side opposite said tibial top side, said tibial bottom side connected to said tibial top side by two tibial sloped sides, said dovetailed at least one tibial attachment means is one third of an inch deep between said tibial top side and said tibial bottom side, two tenths of an inch wide at said tibial top side of said at least one tibial attachment means, and form 60 degree angles between said two tibial sloped sides form and said tibial fixation surface, a femoral prosthesis, a femoral fixation surface on said femoral prosthesis being adapted to be positioned on the femoral condyle, said femoral fixation surface having at least one femoral attachment means for securing said femoral prosthesis to the femoral condyle, said at least one femoral attachment means extend from said femoral fixation surface to be embedded in the femoral condyle, said at least one femoral attachment means is dovetailed in structure, with femoral top side of said at least one femoral attachment means being that which is directly in contact with the femoral prosthesis, a femoral bottom side opposite said femoral top side, said femoral bottom side connected to said femoral top side by two femoral sloped sides, said dovetailed at least one femoral attachment means is about one third of an inch deep between said femoral top side and said femoral bottom side, about two tenths of an inch wide at said femoral top side of said at least one femoral attachment means, and form about 60 degree angles between said two femoral sloped sides form and said femoral fixation surface, said femoral prosthesis having a at least one hole, said at least one hole provided for attachment elements, a bearing member supported by said tibial prosthesis for engaging said femoral prosthesis in weight bearing relationships, said tibial prosthesis having a bearing member fixation surface consisting of a central recess with at least one adjoining recess, said central recess to receive said bearing member, and said at least one adjoining recess to each receive one of at least one clip member, said at least one clip member being attached to said bearing member.

16. The method of prosthesis implantation whereby:

the tibial plateau is resected to form at least one tibial groove so as to receive each tibial attachment means of a tibial prosthesis to secure said tibial prosthesis to the tibial plateau, the femoral condyle is resected to form at least one femoral groove so as to receive each femoral attachment means of a femoral prosthesis to secure said femoral prosthesis to the femoral condyle, said tibial attachment means of said tibial prosthesis is inserted into the at least one tibial groove resected in the tibial plateau, said femoral attachment means of said femoral prosthesis is inserted into the at least one femoral groove resected in the femoral condyle, a bearing member is inserted into a central recess on said tibial prosthesis and is supported by said tibial prosthesis for engaging said femoral prosthesis in weight bearing relationships thereby enabling the implantation of the prosthesis.

17. The method of prosthesis implantation whereby:

the tibial plateau is resected to form at least one dovetailed tibial groove so as to receive each dovetailed tibial attachment means of a tibial prosthesis to secure said tibial prosthesis to the tibial plateau, the femoral condyle is resected to form at least one dovetailed femoral groove so as to receive each dovetailed femoral attachment means of a femoral prosthesis to secure said femoral prosthesis to the femoral condyle, said tibial attachment means of said tibial prosthesis is inserted into the at least one dovetailed tibial groove resected in the tibial plateau, said femoral attachment means of said femoral prosthesis is inserted into the at least one dovetailed femoral groove resected in the femoral condyle, a bearing member is inserted into a central recess on said tibial prosthesis and is supported by said tibial prosthesis for engaging said femoral prosthesis in weight bearing relationships, said tibial prosthesis having a bearing member fixation surface consisting of a central recess with at least one adjoining recess, said central recess to receive said bearing member, and said at least one adjoining recess to each receive one of at least one clip member, said at least one clip member being attached to said bearing member thereby enabling the implantation of the prosthesis.

* * * * *